United States Patent [19]

Bär et al.

[11] Patent Number: 5,661,772
[45] Date of Patent: Aug. 26, 1997

[54] X-RAY DIAGNOSTICS APPARATUS CAPABLE OF PRODUCING CT IMAGES AND FLUOROSCOPIC IMAGES

[75] Inventors: Ulrich Bär, Neunkirchen; Knut Imhof, Herzogenaurach, both of Germany

[73] Assignee: Siemens Aktiengesellschaft, Munich, Germany

[21] Appl. No.: 658,599

[22] Filed: Jun. 5, 1996

Related U.S. Application Data

[63] Continuation of Ser. No. 625,207, Apr. 1, 1996.
[51] Int. Cl.$^6$ .................................................. H05G 1/06
[52] U.S. Cl. ............................ 378/20; 378/195; 378/208
[58] Field of Search .................................. 378/190, 195, 378/198, 208, 209, 177, 180, 4

[56] References Cited

U.S. PATENT DOCUMENTS 5,159,623  10/1992  Niepel ............................. 378/197
5,329,567  7/1994  Ikebe ............................... 378/195

FOREIGN PATENT DOCUMENTS 42 16 983 A1  12/1993  Germany .

*Primary Examiner*—Don Wong
*Attorney, Agent, or Firm*—Hill, Steadman & Simpson

[57] ABSTRACT

An x-ray diagnostics system includes an apparatus for producing computed tomography images and an apparatus for producing x-ray fluoroscopic images, and a common support system for an examination subject allocated both to the computed tomography apparatus and to the fluoroscopy apparatus. The support system includes a base movable along a guide rail between a first position allocated to the computed tomography apparatus and a second position allocated to the fluoroscopy apparatus.

10 Claims, 4 Drawing Sheets

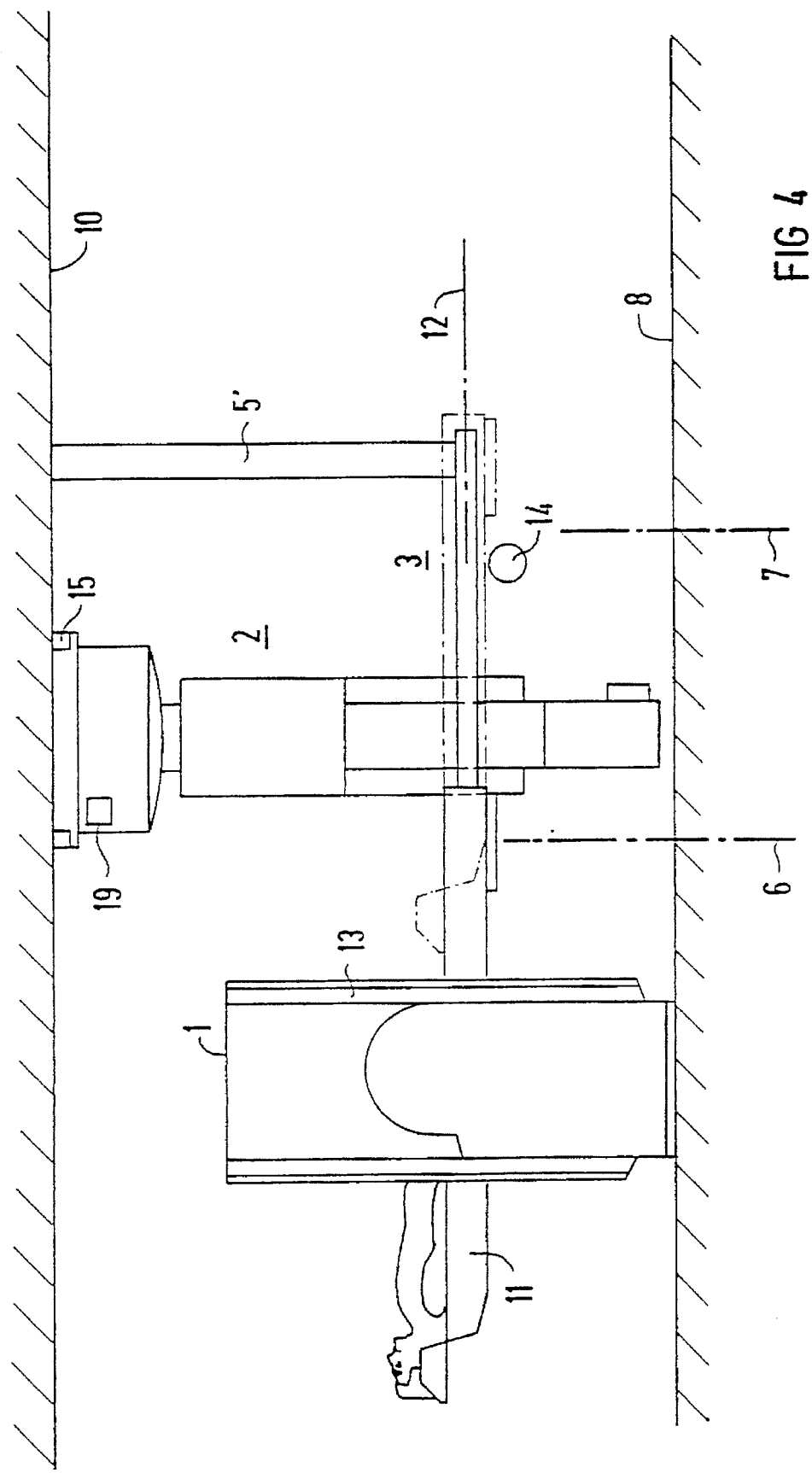

X-RAY DIAGNOSTICS APPARATUS CAPABLE OF PRODUCING CT IMAGES AND FLUOROSCOPIC IMAGES

PRIOR APPLICATION DATA

The present application is a continuation of application Ser. No. 08/625,207, filed Apr. 1, 1996. The present application claims the benefit of that filing date under 35 U.S.C. §120.

BACKGROUND OF THE INVENTION

1. Field of the Invention

The present invention is directed to an x-ray diagnostic apparatus operable in a tomography mode, for producing a CT image, and operable in an x-ray fluoroscopic mode, for producing fluoroscopic images.

2. Description of the Prior Art

X-ray diagnostics systems which have the capability of producing both CT images and x-ray fluoroscopic images are particularly useful when, during an examination of a patient or during a surgical procedure being performed on a patient, both types of exposures are desirable, and must be prepared in the same room.

German OS 42 16 983 discloses a computer tomography apparatus wherein the patient bed is stationary, and the housing of the tomography apparatus is linearly displaced relative to the patient bed with appropriate guide means, in order to avoid inertial forces acting on the patient as would occur during acceleration and deceleration of the patient bed, if the patient bed were movable.

U.S. Pat. No. 5,159,623 discloses a medical apparatus for obtaining angiography exposures, wherein the base of the patient support plate is stationary, and the exposure unit, composed of an x-ray source and a radiation receiver, is spatially adjustable by means of a C-arm, the exposure unit also being adjustable relative to the C-arm itself.

SUMMARY OF THE INVENTION

It is an object of the present invention to provide an x-ray diagnostics installation which is capable of optionally producing either a computed tomography image or x-ray fluoroscopic images, wherein both the tomography exposures and the fluoroscopic exposure can be prepared with the same installation, and the installation being economically manufacturable and occupying little space.

The above object is achieved in accordance with the principles of the present invention in an x-ray diagnostics system having means for producing a computed tomography image of an examination subject and means for producing x-ray fluoroscopic images of the same subject, and having a common bearing means for the examination subject allocated both to the means for producing a computed tomography image and to the means for producing fluoroscopic images, and wherein the bearing means has a base supported on a guide rail for permitting the bearing means to be adjustable along the guide rail from a first position allocated to the means for producing a computed tomography image into a second position allocated to the means for producing x-ray fluoroscopic images.

An advantage achieved by the apparatus of the invention is that the support means for the examination subject are allocated in common to both the computer tomography image producing components and the fluoroscopic image producing components, by means of movement between the aforementioned first and second positions. Since the patient support moves along guide rails between the first and second positions, complicated and expensive and space-consuming components for adjusting the respective positions of the tomography apparatus and the fluoroscopic apparatus relative to the subject are not necessary. This results in the overall system being economic to manufacture and occupying as little space as possible.

DESCRIPTION OF THE DRAWINGS

FIG. 4 is a side view of a further embodiment of an x-ray diagnostics system constructed in accordance with the principles of the present invention, with the patient support mounted at the ceiling.

DESCRIPTION OF THE PREFERRED EMBODIMENTS

Figure 3:
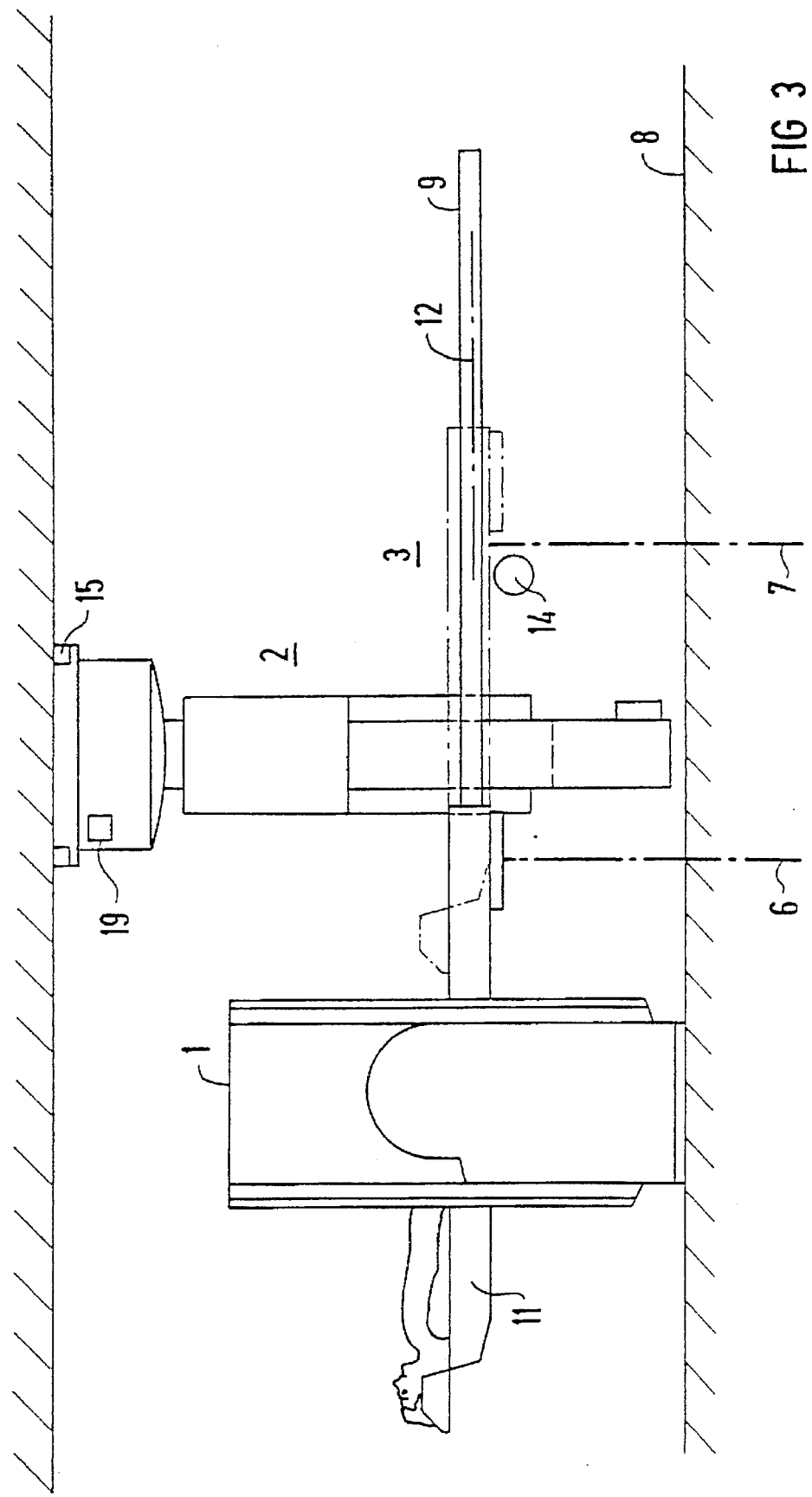
FIG. 3 is a side view of a further embodiment of an x-ray diagnostics system constructed in accordance with the principles of the present invention, with the patient support mounted at a wall, instead of at the floor as in FIG. 1.

In all of the Figures, an x-ray diagnostics system is shown having a computed tomography apparatus generally designated 1, which produced computed tomography images of an examination subject in a known manner. The computed tomography apparatus 1 is a portion of the overall x-ray diagnostics system, which also includes an x-ray fluoroscopy apparatus generally designated at 2, such an angiography apparatus. The x-ray fluoroscopy apparatus 2 produces x-ray fluoroscopic images in a known manner.

a common support system 3 for the examination subject is provided both for the computed tomography apparatus 1 and for the fluoroscopy apparatus 2. This support system 3 includes a base 5 movable along guide rails 4. The support system 3 is adjustable in position along the guide rails 4 from a first position 6, allocated to the computed tomography apparatus 1, into a second position 7, allocated to the fluoroscopy apparatus 2. Preferably the guide rails 4 are disposed on the floor 8 of the examination room, and the guide rails 4 are preferably arranged in channels in the floor 8 so that the top surface of the guide rails 4 is flush with the surface of the floor 8. Alternatively, however, the guide rails 4 can be disposed at the wall 9 or the ceiling 10 of the examination room, as respectively shown in FIGS. 3 and 4.

Operating personnel can adjust the support system 3 between the first and second positions 6 and 7 either manually or in an assisted manner, such as by means of an electromechanical assist apparatus. Preferably, the support system 3 has suitable engagement elements for fixing the position of the support system 3 respectively in the two positions 6 and 7, so that the positions 6 and 7 are defined.

Figure 1:
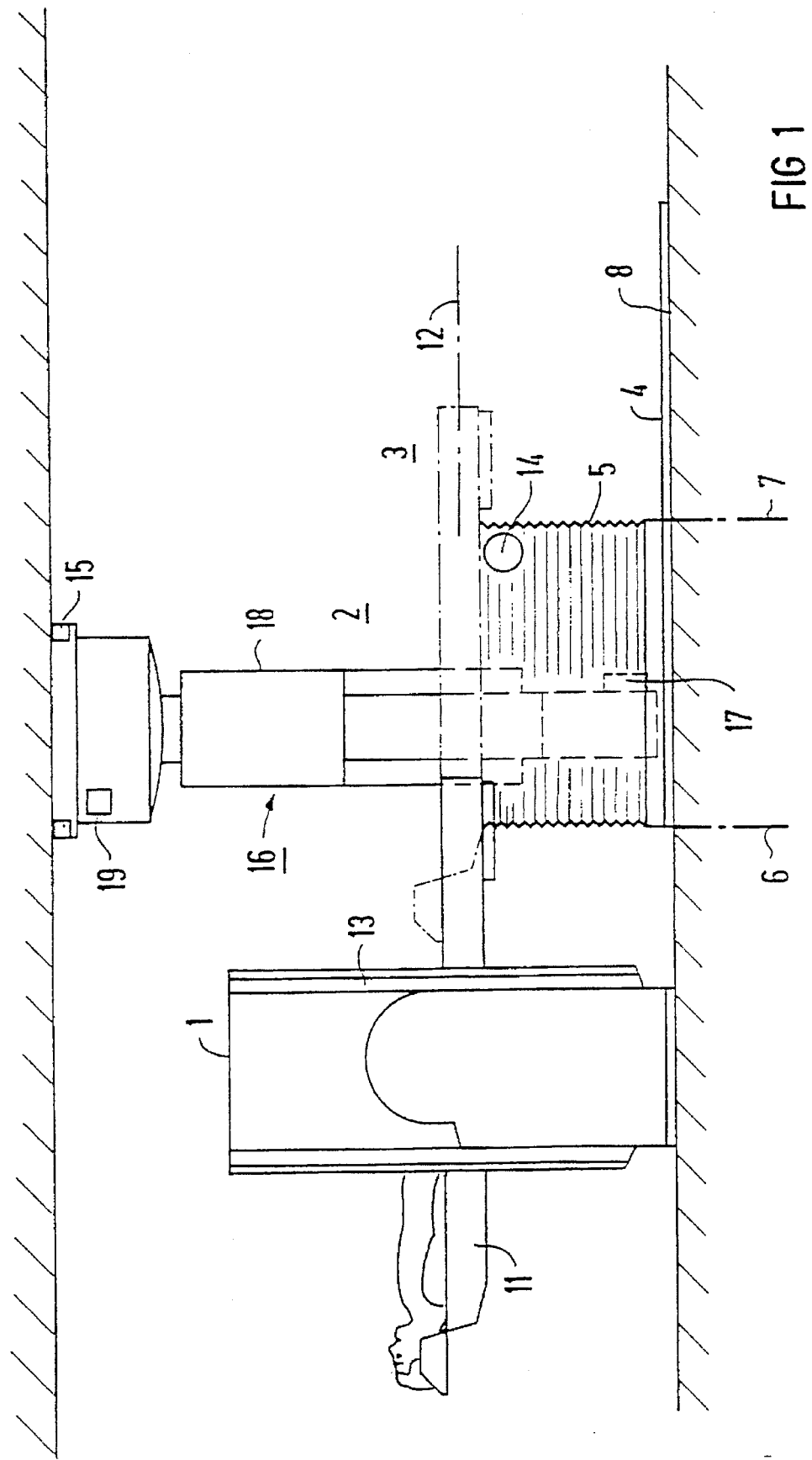
FIG. 1 is a side view of an x-ray diagnostics system constructed in accordance with the principles of the present invention, with the patient support disposed in a first position for producing computed tomography images.
Figure 2:
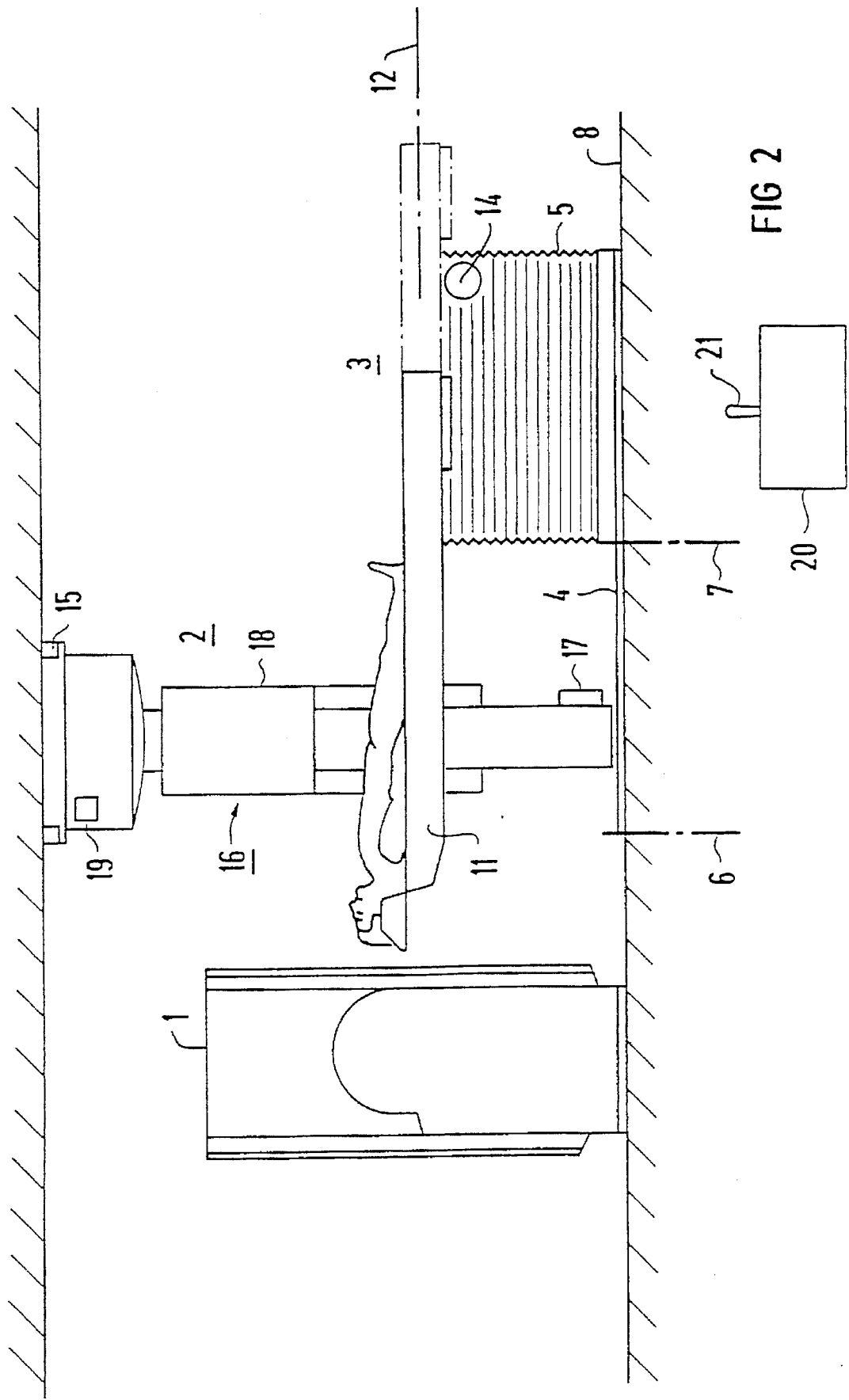
FIG. 2 shows the x-ray diagnostics system of FIG. 1 with the patient support disposed in a second position for producing x-ray fluoroscopic images.

In FIG. 1, the support system 3 is shown in the first position 6, allocated to the computed tomography apparatus 1.

The support system 3 has a support plate 11 which is adjustable along its longitudinal axis 12 into a central opening 13 of the computed tomography apparatus 1, for example by means of a controllable electromechanical positioner 14. Computed tomography exposures can thus be made with the patient in this position. Preferably, for this purpose the support plate 11 is height-adjustable at the base 5. It should be noted that the fluoroscopic apparatus 2 (i.e., the angiography apparatus) is located in a standby position, remote from the support system 3, during the preparation of a tomographic exposures, so that it is not disturb the preparation of the tomographic exposures.

For the preparation of fluoroscopic images, such as angiography exposures, the support system 3 is moved to the second position 7. For example, the fluoroscopic apparatus 2 can be adjusted from the aforementioned standby position into an exposure position along ceiling rails, in at least one direction perpendicular to the longitudinal axis 12. In the exposure position of the fluoroscopic apparatus 2, an exposure unit 16, composed of an x-ray source 17 and a radiation receiver 18, is then allocated to the bearing plate 11 and thus to the examination subject. Another electromechanical positioner 19 can be provided for accomplishing this adjustment.

Preferably the control of the electromechanical positioners 14 and 19 ensues via a control unit 20 having a joystick 21. The operation of the overall x-ray diagnostics system is thus considerably simplified. The control of the electromechanical positioners 14 and 19 can be undertaken in a manner such that, in the second positions of the base 5, the support plate 11 is adjusted to the left or to the right by movement of the joystick 21 respectively to the left or right, as seen from the point of view of the operator. Further, when producing fluoroscopic images, the fluoroscopic apparatus 2 (i.e., the angiography apparatus) is moved in a direction toward the patient support plate 11 by adjusting the joystick 21 in a direction toward the operator, and moved away from the support plate 11 when the joystick 21 is moved in a direction away from the operator.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray-diagnostics system comprising:

means for producing a computed tomography image of an examination subject;

means, separate from said means for producing a computed tomography image, for producing fluoroscopic images of said examination subject;

a support system for said examination subject shared in common by said means for producing a computed tomography image and said means for producing fluoroscopic images, said support system comprising a base, a guide rail on which said base is movably mounted, and means for moving said base along said guide rail from a first position wherein said examination subject is positioned for producing said computed tomography image and a second position wherein said patient is positioned for producing said fluoroscopic images.

2. An x-ray diagnostics system as claimed in claim 1 for use in an examination room, and wherein said guide rail is disposed at a floor of said examination room.

3. An x-ray diagnostics system as claimed in claim 2 wherein said guide rail is recessed in said floor.

4. An x-ray diagnostics system as claimed in claim 1 for use in an examination room, and wherein said guide rail is disposed at a wall of said examination room.

5. An x-ray diagnostics system as claimed in claim 1 for use in an examination room, and wherein said guide rail is disposed at a ceiling of said examination room.

6. An x-ray diagnostics system as claimed in claim 1 comprising means for temporarily engaging said support system in said first position or said second position.

7. An x-ray diagnostics system as claimed in claim 1 wherein said support system includes a support plate having a longitudinal axis, and electromechanical means for adjusting said support plate along said longitudinal axis, wherein said means for producing fluoroscopic images includes an x-ray exposure unit and electromechanical means for spatially adjusting said x-ray exposure unit, and a joystick for controlling respective movements of said support plate and said x-ray exposure unit when said support system in said second position.

8. An x-ray diagnostics system as claimed in claim 7 wherein said exposure unit is movable in a direction perpendicular to said longitudinal axis of said support plate.

9. An x-ray diagnostics system as claimed in claim 8 comprising means for adjusting said support plate along said longitudinal axis given a left/right movement of said joystick and for adjusting said x-ray exposure unit along said direction perpendicular to said longitudinal axis given a forward/backward adjustment of said joystick.

10. An x-ray diagnostics system as claimed in claim 1 wherein said means for producing fluoroscopic images of said examination subject comprises means for producing angiography images of said examination subject.

* * * * *